United States Patent [19]

Rosendal

[11] Patent Number: Plant 6,927

[45] Date of Patent: Jul. 18, 1989

[54] EXACUM PLANT 'BEST ROSE'

[75] Inventor: Erik Rosendal, Assens, Denmark

[73] Assignee: L. Daehnfeldt A/S, Odense, Denmark

[21] Appl. No.: 142,590

[22] Filed: Jan. 11, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Olson and Olson

[57] ABSTRACT

A new and distinctive cultivar of exacum plant particularly characterized by its uniquely colored rose-purple petals not seen in exacum before, the petals surrounding bright yellow-gold stamen, the flower set against a dense, moderately dark green foliage, the plant having a rapid, full and compact growth, a floriferous display of rose-purple flowers that have stamens and style and produce seed, and reproduces easily and consistently by cuttings or by seed.

2 Drawing Sheets

BACKGROUND OF THE INVENTION

This invention relates to a new and distinctive cultivar of exacum plant known botanically as exacum affine and known by the cultivar name Best Rose.

This new cultivar was discovered by me as a result of radiation treatment carried out on meristematic tissues of my exacum cultivar Best Blue, and continued successive selection to obtain a new color, grown as a pot plant.

Asexual reproduction by stem cuttings has reproduced the unique features by the new cultivar through successive propagations. Sexual propagation by seed is possible as the flowers are fertile. Seedlings are true to type meaning that seedlings give exactly the same uniform product as cuttings.

The following characteristics distinguish the new exacum from both its parents and other exacum affines commercially known and used in the floriculture industry:

(1) Flowers are single.

(2) Growth rate is equal to other single flowered cultivars.

(3) Growth as potted plant is compact.

(4) The color of the petals of the flower is rose-purple, a color not seen in exacum before.

(5) The flowers have stamens and style and produce seed.

(6) The cultivar reproduces easily with cuttings and also by seed.

(7) The color and appearance of the wilted flower do not disfigure the plant in the same manner as known in blue cultivars.

THE DRAWING

The accompanying color photographs illustrate the overall appearance of this cultivar taken, one, as a face view of the overall plant second, of a close up of the flower and foliage and showing the colors as true as it is reasonably possible to obtain in a colored reproduction of this type.

DESCRIPTION OF THE NEW VARIETY

The following is a detailed description of my new exacum cultivar based on plants produced under experimental growing conditions in glasshouses in Sandager, in Denmark. Color references are made to The Royal Horticultural Society Colour Chart, except where general color terms of ordinary dictionary significance are used.

PARENTAGE

The new variety is a result of radiation treatment carried out on meristematic tissues of my exacum affine cultivar Best Blue, and continued successive selection to obtain a new color.

PROPAGATION

Type cutting: Terminal Shoots or stem segments.

Color:

*Stem.*—144B by internode tinted 61.

Length of internode: 25–36 mm.

Structure: Strong, rounded quadrangular.

Breaking action: Sympodial. One flower terminal at each node and two side shoots.

Time to root: 12–14 days at 21° C. in summer; 12–14 days at 21° C. in winter.

Rooting habit: Dense and fibrous.

Time for shoot development of cuttings: 14 days.

THE PLANT

Form: Upright, with heavy paniculate branching from base to terminal shoots. Potted plant diameter similar to its height.

Habit of growth: Rapid under good light conditions. Growth is compact.

Foliage: Opposite, sessile leaves at the bottom of all nodes.

(1) *Size.*—Average leaf at maturity from 4–4.5 cm. (1.6–1.8 inches) long.

(2) *Shape.*—Cordate to elliptic ovate.

(3) *Tip.*—Acute.

(4) *Base.*—Attenuate.

(5) *Texture.*—Glabrous.

(6) *Margin.*—Entire.

(7) *Color.*—Young foliage top side; 138A. under side; 144A. mature foliage top side; 138A. under side; 144A. petiole; 144B. veins; 145B.

(8) *Veination.*—Three veined from petiole. Middle vein deepest.

THE FLOWER

Flowering habits: The large number of flowers appear clear of the compact foliage where new buds and flowers succeed. The wilted flowers do not disfigure as much as typical with blue cultivars.

Natural flowering season: April–October.

Flower bud: Round, 5–6 mm (0.2–0.24 inch) color 145C.

Flowers borne: Terminal, single at the end of each node.

Quantity: Floriferous.

Petals:

(1) *Shape.*—Round.

(2) *Color.*—186B–186C greyed purple. Reverse: 186C.

(3) *Number.*—5.

(4) *Size.*—8–9 mm (0.32–0.36 inches).

(5) *Flower size.*—15–20 mm (0.6–0.8 inches).

Reproductive organs: Sexual propagation or young tip/stem cuttings.

Disease resistance: No particular increase in resistance to disease observed to date.

I claim:

1. A new and distinct cultivar of exacum affine plant named Best Rose, as shown and described, and particularly characterized by its uniquely colored rose-purple petals never seen in exacum before, the petals surrounding bright yellow-gold stamen to produce a unique flower set against a dense, moderately dark green foliage, the cultivar having a rapid, full and compact growth, a floriferous display of rose-purple flowers that produce seed, and reproduces easily and consistently by cuttings or seed.

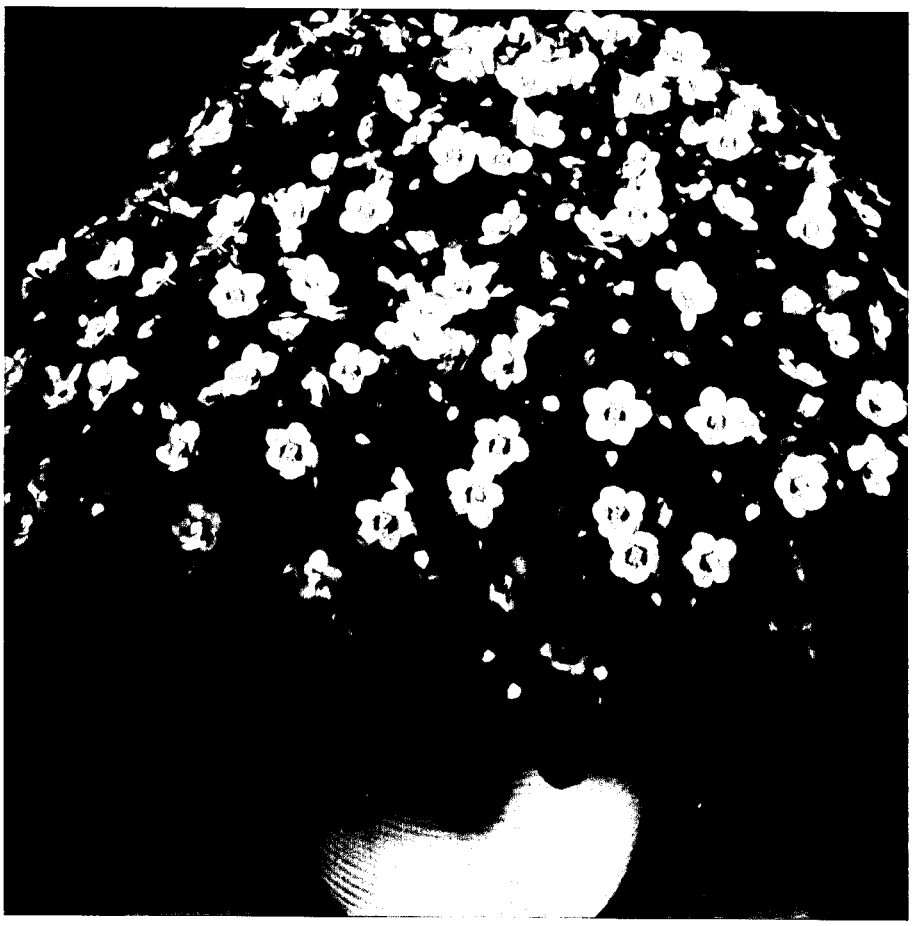

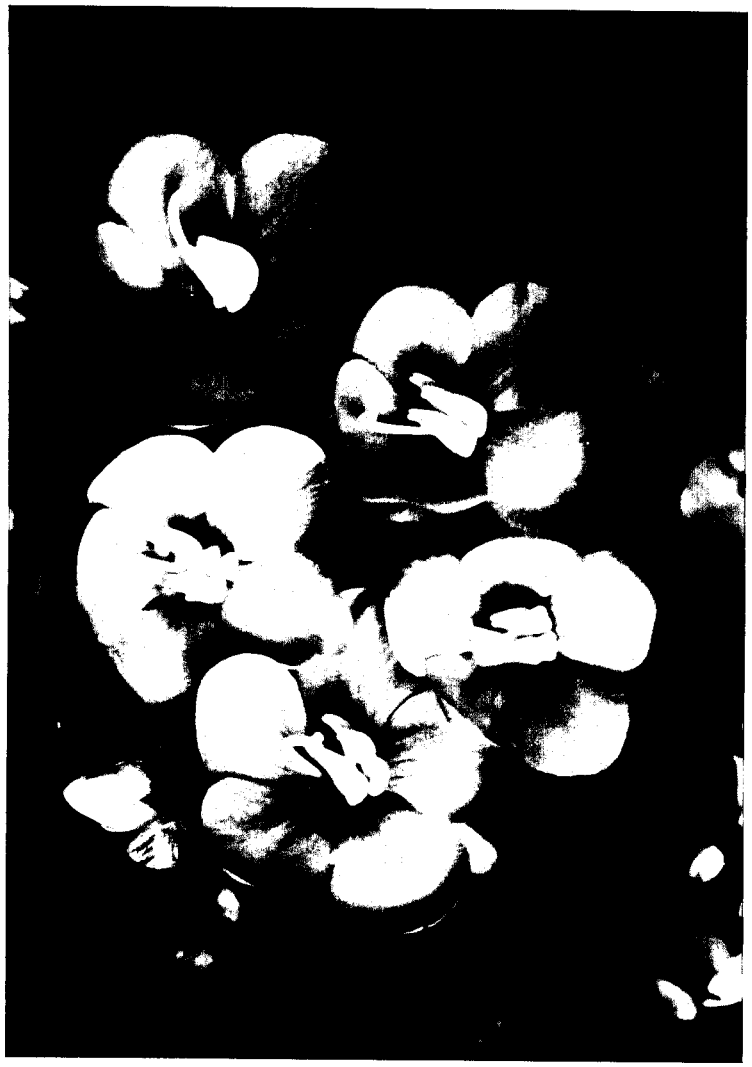

* * * * *